US012708735B2

(12) United States Patent
Fenster et al.

(10) Patent No.: US 12,708,735 B2
(45) Date of Patent: Aug. 18, 2026

(54) SYSTEM AND METHOD FOR REDUCING THE PREVALENCE OF DELIRIUM IN PATIENTS IN AN ISOLATING HEALTHCARE ENVIRONMENT

(71) Applicant: VOICELOVE INC., Dover, DE (US)

(72) Inventors: Tamatha Fenster, Scarsdale, NY (US); Marc Schiffman, Buffalo, NY (US)

(73) Assignee: VOICELOVE INC.

( * ) Notice: Subject to any disclaimer, the term of this patent is extended or adjusted under 35 U.S.C. 154(b) by 1099 days.

(21) Appl. No.: 17/842,466

(22) Filed: Jun. 16, 2022

(65) Prior Publication Data

US 2022/0313942 A1 Oct. 6, 2022

Related U.S. Application Data

(60) Provisional application No. 63/211,416, filed on Jun. 16, 2021.

(51) Int. Cl.

| | |
|---|---|
| ***A61M 21/00*** | (2006.01) |
| ***H04W 4/10*** | (2009.01) |

(52) U.S. Cl.

CPC .............. *A61M 21/00* (2013.01); *H04W 4/10* (2013.01); *A61M 2021/0027* (2013.01); *A61M 2205/3553* (2013.01); *A61M 2205/505* (2013.01)

(58) Field of Classification Search

CPC ... A61M 21/00–02; A61M 2205/3553; H04W 4/10; H04L 65/403–4061

See application file for complete search history.

(56) References Cited

U.S. PATENT DOCUMENTS

| | | | | |
|---|---|---|---|---|
| 2013/0166292 | A1* | 6/2013 | Van Sciver | G10L 13/04 704/235 |
| 2013/0314866 | A1* | 11/2013 | Millman | A61M 21/02 361/679.02 |

(Continued)

*Primary Examiner* — Thaddeus B Cox
(74) *Attorney, Agent, or Firm* — Gearhart Law LLC

(57) ABSTRACT

A method of preventing, reducing, or mitigating hospital-acquired dementia of a patient in an isolating healthcare environment, such as an ICU, is disclosed. The method includes: providing a patient device enabling voice communication between the patient and persons associated with the patient, the patient device comprising a speaker for receiving voice communications, a microphone for playback of voice communication, a touchscreen having an area; the patient device programmed with a walkie-talkie app for voice communication between the patient and persons associated with the patient and configured to communicate with a server over the Internet via an encrypted data link, the persons having other devices programmed with the walkie-talkie app; the server programmed and configured to receive over the encrypted data link and store patient voice communications from the walkie-talkie app of the patient device and to transmit the patient voice communications to the walkie-talkie app of the other devices over the encrypted data link, and to receive over the encrypted data link and store other voice communications from the walkie-talkie app of the other devices and to transmit the other voice communications to the walkie-talkie app of the patient device over the encrypted data link, thereby enabling voice communication between the patient and the persons associated with the patient; the walkie-talkie app programmed and configured to operate on the patient device in a plurality of modes, the plurality of modes including an in-case mode in which most or all of the area of the touchscreen is a push-to-talk button; the patient device encased within an enclosure consisting of a flexible material having a raised tactile feature on a patient-facing side of the enclosure for (Continued)

assisting the patient in locating the push-to-talk button by touch; whereby the enabling of voice communication between the patient and persons associated with the patient being effective to prevent, reduce, or mitigate hospital-acquired dementia of the patient.

4 Claims, 9 Drawing Sheets

(56) References Cited

U.S. PATENT DOCUMENTS

| | | | | |
|---|---|---|---|---|
| 2014/0026101 | A1* | 1/2014 | Pallakoff | G06F 3/0483 715/841 |
| 2015/0105152 | A1* | 4/2015 | Bellinghausen | A63F 13/2145 463/31 |
| 2019/0167930 | A1* | 6/2019 | Cox | A61M 16/0066 |

* cited by examiner

SYSTEM AND METHOD FOR REDUCING THE PREVALENCE OF DELIRIUM IN PATIENTS IN AN ISOLATING HEALTHCARE ENVIRONMENT

CROSS-REFERENCE TO RELATED APPLICATION

This application claims the benefit of U.S. Provisional Patent Application No. 63/211,416, filed Jun. 16, 2021, the entirety of which is hereby incorporated by reference for all purposes.

BACKGROUND OF THE SUBJECT TECHNOLOGY

Some hospital patients must be maintained in a state of substantial isolation, while simultaneously suffering a serious or life-threatening illness. For example, many COVID-19 patients must be isolated to prevent the spread of that contagious disease, while having to endure a difficult course of treatment and the possibility of his or her medical situation taking a turn for the worse. Such patients may be bedridden or otherwise lack mobility.

Patients experiencing stays in an intensive care unit ("ICU"), institutionalization, or stays in nursing homes, rehabilitation facilities, and hospices, face significant risks as a consequence of the isolating healthcare environment ("IHE"). It should be understood that references herein to the ICU environment are applicable to other IHEs.

Delirium, an acute and fluctuating disorder of attention and cognition, is a common and costly complication of illness, acute trauma, and surgery in hospitalized patients often resulting in prolonged mechanical ventilation, longer lengths of stay, and long-term disability. (References 1-3 (refer the Endnotes section for all background references.) Intensive care unit ("ICU") delirium is highly prevalent, affecting 1 in 3 critically ill patients (1,4,5) with older adults (>65 years) being especially vulnerable. (6,7) The poor clinical outcomes associated with delirium have also been identified to have a "dose-dependent" relationship—for each day an ICU patient is delirious, the risk of remaining in the hospital increases by 20%, 6-month and 1-year mortality increases by 10%, and long-term cognitive impairment (e.g., ADRD) more than doubles. (1,8-11) Delirium increases a patient's risk of developing long-term cognitive impairment akin to AD/ADRD. Older ICU survivors, and especially those with delirium, have a 12.5-fold increased incidence of newly diagnosed ADRD. (14) Over 30% of patients without preexisting ADRD have persistent cognitive impairment over a year after hospital discharge. (15) In addition, delirium accelerates cognitive decline in AD/ADRD patients. Patients with underlying dementia are 2.5-4.7 times more likely to develop delirium. 14 AD/ADRD patients who develop delirium have a markedly overall increase in adverse outcomes including rate of cognitive decline, institutionalization, and death following an episode of delirium compared to those without pre-existing AD/ADRD. (14,16, 17)

The societal costs of delirium are substantial, and include increased disability, lost work, and institutionalization, among other costs. (12,13) The design and testing of prevention and management strategies for ICU delirium, thereby increasing the number of delirium-free days, is critical to improving both short and long-term outcomes for critically ill patients.

IHE-induced delirium in an ICU patient may lead to complications including an increased risk for dementia and related agitation and consequent action or even violence against nurses or other attending healthcare professionals.

The multicomponent ABCDEF ("A2F") Bundle has the best success at decreasing ICU delirium among known pharmacologic and nonpharmacologic interventions. (18) The A2F Bundle is a comprehensive roadmap to align and coordinate care processes regardless of the underlying illness pathology, includes a specific focus on delirium assessment and management as a component of a bundled approach to achieve patients who are awake, cognitively engaged, and mobile with family members engaged as partners with the ICU team. (19) "Family members" in this way can include both biologic family members and/or loved ones, spiritual advisors, clergy, friends, caregivers, social workers, celebrities, and other persons who are valuable support persons within the patient's life. The components of the A2F bundle are Assess, prevent, and manage pain, Both spontaneous awakening and breathing trials, Choice of analgesia and sedation, Delirium: assess, prevent, and manage, Early mobility and exercise, and Family engagement and empowerment. While each of these bundle components are individually successful, the most effective way to improve in-hospital quality of care and survivorship following hospital discharge is compliance with all components of the A2F bundle whenever possible. (20,21) Patients with complete A2F bundle performance have a 40% lower likelihood of delirium the next day with increasing proportions of bundle components completed equating to greater benefit. (20,22)

Family engagement, an essential component of the A2F bundle, may be restricted due to restricted or low-flexibility visitation. This is associated with increased delirium among ICU patients. (23,24) For patients, the ICU environment is frightening and unfamiliar. Family engagement involves family presence and involvement in ICU care and decision making and helps to keep patients and families as the center and focus of care. More flexible ICU visitation hours are associated with a 60% lower frequency of delirium, lower severity of patient anxiety, and greater family satisfaction. (24)

Likewise, protocolized family involvement is associated with decreased length of stay without affecting patient mortality. (25) However, implementing family engagement is a major challenge for most healthcare facilities. Before the coronavirus 2019 (COVID-19) pandemic, family engagement was only implemented in 63% of ICUs. Due to severe visitation restrictions, family engagement is now being implemented in less than 20% of ICUs. (26) Specific to COVID-19 ICU patients, severely restricted family visitation is associated with increased delirium. (23) The short and long-term effects of these policies put patients at risk for increased anxiety, delirium, and cognitive impairment. Family engagement during critical illness is especially valuable for preparing patients and family members for a potentially prolonged and complicated ICU recovery following hospital discharge. (27-29) Facilitating engagement promotes health and recovery of both patients and their support systems. (30)

Thus, interventions enabling expanded family engagement have the potential to significantly improve both patient and family outcomes including less dementia, anxiety, depression, post-traumatic stress symptoms, long-term grief, and AD/ADRD.

There is a critical unmet need to enhance family engagement during critical illness via alternative modalities. The hospital experience can have profound effects on outcomes for both patients and caregivers and communication is critical at every step of a patient's clinical course. Direct, understandable, and sustained communication with family members and key decision-makers is important to develop trust and understanding between clinical events and patient values. (31) When such communication is included within daily ICU rounds, families report a sense of understanding, inclusion, and respect that bodes well for the satisfaction of both care teams and family members. (32) Additionally, family involvement decreases the risk of subsequent family trauma including post-traumatic stress symptoms and anxiety. (32) This is especially valuable as many patients depend on continued family support throughout their recovery process following hospital discharge. A healthy and supported family unit promotes the continued health and recovery of both patients and their support systems. Currently, ICU workers (e.g., physicians, critical support staff) spend little time in direct patient contact. (33) Under these circumstances, addressing personal needs and facilitating communication presents a significant challenge.

Attempts at utilizing common communication technologies such as cellphones and iPads to connect ICU patients with family and care providers, etc., present significant challenges. Typically, use of these common devices requires a nurse or other healthcare professional to attend at the patient's bedside and operate the device to, for example, dial the phone, activate Apple Facetime, or otherwise establish and maintain the communication. This is a demand on the time and energy of the healthcare professional, and exposes the professional to possible contagion, requiring use of scarce personal protective equipment (PPE)—at a time when these resources continue to be limited.

Therefore, there is a need for a communication device and system that is made available to, and operable by, an ICU patient, to mitigate the deleterious effects of the ICU stay. The patient may be significantly impaired in physical activity and visual acuity (low-vision or blind).

The present inventors have previously experimented with providing a commercially available child's walkie-talkie device at a COVID patient's bedside, the device in a rigid case attached with straps to the patient's bed rail. The case had formed therein a tactilely detectable feature for manually operating the "talk" button of the device, which was disposed under the feature. The purpose of providing this device was to enable voice communication between the infected and isolated patient, and the patient's family and hospital staff, during a time when in-person visitation by family was forbidden, and when in-person attendance of hospital staff would consume scarce personal protective equipment. This device and arrangement were found to be deficient in several areas including security, utility and operational flexibility.

Endnotes. 1: Salluh, J. I. et al. Outcome of delirium in critically ill patients: systematic review and meta-analysis. Bmj 350, h2538, doi:10.1136/bmj.h2538 (2015). 2: Brummel, N. E. et al. Frailty and Subsequent Disability and Mortality among Patients with Critical Illness. Am J Respir Crit Care Med 196, 64-72, doi:10.1164/rccm.201605-09390C (2017). 3: Brummel, N. E. et al. Delirium in the ICU and subsequent long-term disability among survivors of mechanical ventilation. Critical care medicine 42, 369-377, doi:10.1097/CCM.0b013e3182a645bd (2014). 4: Pisani, M. A., McNicoll, L. & Inouye, S. K. Cognitive impairment in the intensive care unit. Clinics in chest medicine 24, 727-737, doi:10.1016/s0272-5231(03)00092-3 (2003). 5: Krewulak, K. D., Stelfox, H. T., Leigh, J. P., Ely, E. W. & Fiest, K. M. Incidence and Prevalence of Delirium Subtypes in an Adult ICU: A Systematic Review and Meta-Analysis. Crit Care Med 46, 2029-2035, doi:10.1097/ccm.0000000000003402 (2018). 6: Inouye, S. K. Delirium in older persons. N Engl J Med 354, 1157-1165, doi:10.1056/NEJMra052321 (2006). 7: Zaal, I. J., Devlin, J. W., Peelen, L. M. & Slooter, A. J. A systematic review of risk factors for delirium in the ICU. Crit Care Med 43, 40-47, doi:10.1097/ccm.0000000000000625 (2015). 8: Ely, E. W. et al. Delirium as a predictor of mortality in mechanically ventilated patients in the intensive care unit. Jama 291, 1753-1762, doi:10.1001/jama.291.14.1753 (2004). 9: Pisani, M. A. et al. Days of delirium are associated with 1-year mortality in an older intensive care unit population. Am J Respir Crit Care Med 180, 1092-1097, doi:10.1164/rccm.200904-05370C (2009). 10: Girard, T. D. et al. Delirium as a predictor of long-term cognitive impairment in survivors of critical illness. Crit Care Med 38, 1513-1520, doi:10.1097/CCM.0b013e3181e47be1 (2010). 11: Pandharipande, P. P. et al. Long-term cognitive impairment after critical illness. N Engl J Med 369, 1306-1316, doi:10.1056/NEJMoa1301372 (2013). 12: Milbrandt, E. B. et al. Costs associated with delirium in mechanically ventilated patients. Crit Care Med 32, 955-962, doi:10.1097/01.ccm.0000119429.16055.92 (2004). 13: Vasilevskis, E. E. et al. The Cost of ICU Delirium and Coma in the Intensive Care Unit Patient. Med Care 56, 890-897, doi:10.1097/mlr.0000000000000975 (2018). 14: Fong, T. G., Davis, D., Growdon, M. E., Albuquerque, A. & Inouye, S. K. The interface of delirium and dementia in older persons. The Lancet. Neurology 14, 823 (2015). 15: Cole, M. G., Ciampi, A., Belzile, E. & Zhong, L. Persistent delirium in older hospital patients: a systematic review of frequency and prognosis. Age and ageing 38, 19-26 (2009). 16: Fong, T. G., Tulebaev, S. R. & Inouye, S. K. Delirium in elderly adults: diagnosis, prevention and treatment. Nature reviews. Neurology 5, 210-220, doi:10.1038/nrneurol.2009.24 (2009). 17: Weiner, M. F. Impact of delirium on the course of Alzheimer disease. Archives of neurology 69, 1639-1640, doi:10.1001/archneurol.2012.2703 (2012). 18: Witlox, J. et al. Delirium in elderly patients and the risk of postdischarge mortality, institutionalization, and dementia: a meta-analysis. Jama 304, 443-451, doi:10.1001/jama.2010.1013 (2010). 19: Ely, E. W. The ABCDEF Bundle: Science and Philosophy of How ICU Liberation Serves Patients and Families. Crit Care Med 45, 321-330, doi:10.1097/ccm.0000000000002175 (2017). 20: Pun, B. T. et al. Caring for Critically Ill Patients with the ABCDEF Bundle: Results of the ICU Liberation Collaborative in Over 15,000 Adults. Crit Care Med 47, 3-14, doi:10.1097/ccm.0000000000003482 (2019). 21: Miller, M. A., Govindan, S., Watson, S. R., Hyzy, R. C. & Iwashyna, T. J. ABCDE, but in that order? A cross-sectional survey of Michigan intensive care unit sedation, delirium, and early mobility practices. Ann Am Thorac Soc 12, 1066-1071, doi:10.1513/AnnalsATS.201501-0660C (2015). 22: Barnes-Daly, M. A., Phillips, G. & Ely, E. W. Improving Hospital Survival and Reducing Brain Dysfunction at Seven California Community Hospitals: Implementing PAD Guidelines Via the ABCDEF Bundle in 6,064 Patients. Crit Care Med 45, 171-178, doi:10.1097/ccm.0000000000002149 (2017). 23: Pun, B. T. et al. Prevalence and risk factors for delirium in critically ill patients with COVID-19 (COVID-D): a multicentre cohort study. The Lancet. Respiratory medicine, doi:10.1016/s2213-2600(20)30552-x (2021). 24: Nassar Junior, A. P. et al. Flexible Versus Restrictive Visiting Policies in ICUs: A Systematic Review and Meta-Analysis. Crit Care Med 46, 1175-1180, doi:10.1097/ ccm.0000000000003155 (2018). 25: Lee, H. W., Park, Y., Jang, E. J. & Lee, Y. J. Intensive care unit length of stay is reduced by protocolized family support intervention: a systematic review and meta-analysis. Intensive Care Med 45, 1072-1081, doi:10.1007/s00134-019-05681-3 (2019). 26: Liu, K. et al. ABCDEF Bundle and Supportive ICU Practices for Patients With Coronavirus Disease 2019 Infection: An International Point Prevalence Study. Crit Care Explor 3, e0353, doi:10.1097/cce.0000000000000353 (2021). 27: Harvey, M. A. & Davidson, J. E. Postintensive Care Syndrome: Right Care, Right Now . . . and Later. Critical care medicine 44, 381-385, doi:10.1097/ccm.0000000000001531 (2016). 28: Davidson, J. E. et al. Guidelines for Family-Centered Care in the Neonatal, Pediatric, and Adult ICU. Critical care medicine 45, 103-128, doi:10.1097/ccm.0000000000002169 (2017). 29: Davidson, J. E., Jones, C. & Bienvenu, 0. J. Family response to critical illness: postintensive care syndrome-family. Crit Care Med 40, 618-624, doi:10.1097/CCM.0b013e318236ebf9 (2012). 30: Committee on the Learning Health Care System in America; Institute of Medicine; Smith M, Saunders R, Stuckhardt L, et al., editors. Best Care at Lower Cost: The Path to Continuously Learning Health Care in America. Washington (DC): National Academies Press (US); 2013 May 10. 7, Engaging Patients, Families, and Communities. Available from: https://www.ncbi.nlm.nih.gov/books/NBK207234/. 31: Curtis, J. R. et al. Missed opportunities during family conferences about end-of-life care in the intensive care unit. Am J Respir Crit Care Med 171, 844-849, doi:10.1164/rccm.200409-12670C (2005). 32: Xyrichis, A. et al. Interventions to promote family member involvement in adult critical care settings: a systematic review. BMJ Open 11, e042556, doi:10.1136/bmjopen-2020-042556 (2021). 33: Butler, R. et al. Estimating Time Physicians and Other Health Care Workers Spend with Patients in an Intensive Care Unit Using a Sensor Network. The American journal of medicine 131, 972.e979-972.e915, doi:10.1016/j.amjmed.2018.03.015 (2018). 34: Lewis, J., Utesch, B. & Maher, D. Measuring Perceived Usability: The SUS, UMUX-LITE, and AltUsability. International Journal of Human-Computer Interaction 31, 150625095336004, doi:10.1080/10447318.2015.1064654 (2015). 35: Kortum, P. & Sorber, M. Measuring the Usability of Mobile Applications for Phones and Tablets. International Journal of Human-Computer Interaction 31, 518-529, doi:10.1080/10447318.2015.1064658 (2015). 36: System Usability Scale (SUS) [Internet]. Available at https://www.usability.gov/how-to-and-tools/methods/system-usability-scale.html. Accessed on Mar. 19, 2022. 37: Association for the Advancement of Medical Instrumentation (AAMI) Human Factors Engineering Committee. Design of Medical Devices. Arlington, Va.: 2009:445. 38: Weinger, M., Wiklund, M. & Gardner-Bonneau, D. Handbook of Human Factors in Medical Device Design. Boca Raton, Fla.: CRC Press/Taylor Francis 2011. 39: Holtzblatt, K. & Jones, S. Contextual inquiry: Principles and practice. In: Schuler D, Namioka A, eds. Participatory design: Principles and practice Hillsdale, N.J.: Erlbaum 1993. 40: Unertl, K. M., Weinger, M. B., Johnson, K. B. & Lorenzi, N. M. Describing and modeling workflow and information flow in chronic disease care. Journal of the American Medical Informatics Association: JAMIA 16, 826-836, doi:10.1197/jamia.M3000 (2009). 41: Girard, T. D. et al. Haloperidol and Ziprasidone for Treatment of Delirium in Critical Illness. The New England journal of medicine, doi:10.1056/NEJMoa1808217 (2018). 42: Hughes, C. G. et al. Dexmedetomidine or Propofol for Sedation in Mechanically Ventilated Adults with Sepsis. The New England journal of medicine 384, 1424-1436, doi:10.1056/NEJMoa2024922 (2021). 43: Harris, P. A. et al. Research electronic data capture (REDCap)—a metadata-driven methodology and workflow process for providing translational research informatics support. J Biomed Inform 42, 377-381, doi:10.1016/j.jbi.2008.08.010 (2009). 44: Sessler, C. N. et al. The Richmond Agitation-Sedation Scale—Validity and reliability in adult intensive care unit patients. American Journal of Respiratory and Critical Care Medicine 166, 1338-1344, doi:10.1164/rccm.2107138 (2002). 45: Prigerson, H. G. et al. Prolonged grief disorder: Psychometric validation of criteria proposed for DSM-V and ICD-11. PLoS Med 6, e1000121, doi:10.1371/journal.pmed.1000121 (2009).

SUMMARY OF THE SUBJECT TECHNOLOGY

The subject technology concerns systems and methods for preventing, reducing, and/or mitigating hospital-acquired dementia and/or agitation of a patient in an isolating healthcare environment ("IHE") (for example, an ICU, nursing home, rehabilitation facility, hospice, residential mental health facility, psychiatric hospital, or similar), by providing devices and systems enabling the patient to safely and securely communicate with family, friends, professionals, celebrities, and other persons associated with the patient, under control of the patient.

According to a non-limiting embodiment of the subject technology, the present inventors have created a smart device app (the "VoiceLove app") that turns mobile phones into easy-to-use walkie talkies with unique, encrypted channels. This HIPAA compliant application can be used across hospital care settings, but is particularly valuable in the ICU when impairments in patient communication are especially pronounced. Designed to facilitate communication between patients, their families, and care providers, VoiceLove provides an effective solution to enhancing family engagement, thereby mitigating the effects of the ICU state on the patient's mentation and state of health. VoiceLove also enables attention to the IHE patient's spiritual needs, enabling communication with clergy and family in ministering and attending to last needs and prayers.

The VoiceLove application turns mobile phones into secure walkie talkies that allow patients, their loved ones, and healthcare workers to speak over a predesignated channel. Devices are connected on the same channel using unique paring IDs. Each device is associated with individual login credits. There is no limit on users within a channel. The encrypted, app to app communication allows users to send and receive encrypted voice messages at the touch of a button. Channel codes eliminate the need to release personal information. The application has a case mode that turns the screen into one large button to facilitate ease of use, so patients only touch the screen to speak on the walkie talkie channel.

VoiceLove is HIPAA compliant. It has secure, voice-only functionality to mitigate privacy concerns and security risks while improving comfort and communication.

VoiceLove provides emotional value by assuring patients they are never alone and always connected with loved ones. It enhances the use experience by providing an instant one-touch connection to communicate seamlessly regardless of personal abilities via walkie-talkie functionality.

VoiceLove has multiple uses throughout the medical setting. By eliminating the need for an intermediary, implementation of VoiceLove reduces communication lags and keeps all parties well-informed. The burden on nursing staff is reduced and the number incoming calls to nurses and staff are lower. It allows for direct communication, even from within the operating room, and dramatically improves hospital workflow and protects staff from hazardous contact. It enables instant consent to prevent surgeons and operating rooms from extended wait times. It also enables staff-to-staff contact. Hospital staff may be issued devices, which may be "bricked" devices, with the app of the subject technology, and may be assigned dedicated channels to enable staff-to-staff communication.

VoiceLove also provides a protective case for use in the hospital environments. The single use, biodegradable, anti-bacterial case was designed for protection of privacy and safety. It prevents inadvertent use of video recording or accidental outgoing messages. When the phone is in case mode, a large, raised "hold to talk" button allows the user to play audio messages as they are received. The button also makes the VoiceLove app easy to use for people with disabilities (i.e., poor eyesight).

In sum, Voice Love allows for direct communication with the patient, even from within the operating room, and dramatically improves hospital workflow and protects staff from hazardous contact. It eliminates the need for an intermediary to facilitate communication. It has secure, voice-only functionality to mitigate privacy concerns and security risks while improving comfort and communication. It relieves duties of nursing staff and lowers incoming calls to nurses and staff. It enables instant consent to prevent surgeons and operating rooms from extended wait times. It enhances the in-patient experience with instant, one-touch connection to communicate seamlessly regardless of personal abilities using the walkie-talkie functionality. Travel issues, video connectivity, socioeconomic status, infectious disease, and other restrictions are no longer limitations of connecting a patient to his or her support network.

The Voice Love system has numerous applications outside the context of preventing dementia in an isolating hospital environment. For example, a newborn in a neonatal intensive care unit may be assigned a channel on the Voice Love app to communicate with mother, family, friends, heath care providers, and others, which would mitigate the prevalence of neonatal pain and, with respect to the mother, postpartum depression. Entirely outside the hospital context, a member of the armed forces may be assigned a channel to improve their communications with family, friends, and others, and this connectivity and social support would continue if the soldier is wounded and hospitalized.

According to an aspect of the subject technology, a method of preventing, reducing, or mitigating hospital-acquired dementia of a patient in an isolating healthcare environment, comprising the steps of: providing a patient device enabling voice communication between the patient and persons associated with the patient, the patient device comprising a speaker for receiving voice communications, a microphone for playback of voice communication, a touch-screen having an area; the patient device programmed with a walkie-talkie app for voice communication between the patient and persons associated with the patient and configured to communicate with a server over the Internet via an encrypted data link, the persons having other devices programmed with the walkie-talkie app; the server programmed and configured to receive over the encrypted data link and store patient voice communications from the walkie-talkie app of the patient device and to transmit the patient voice communications to the walkie-talkie app of the other devices over the encrypted data link, and to receive over the encrypted data link and store other voice communications from the walkie-talkie app of the other devices and to transmit the other voice communications to the walkie-talkie app of the patient device over the encrypted data link, thereby enabling voice communication between the patient and the persons associated with the patient; the walkie-talkie app programmed and configured to operate on the patient device in a plurality of modes, the plurality of modes including an in-case mode in which most or all of the area of the touchscreen is a push-to-talk button; the patient device encased within an enclosure consisting of a flexible material having a raised tactile feature on a patient-facing side of the enclosure for assisting the patient in locating the push-to-talk button by touch; whereby the enabling of voice communication between the patient and persons associated with the patient being effective to prevent, reduce, or mitigate hospital-acquired dementia of the patient.

According to a further aspect of the subject technology, the persons associated with the patient are one or more of: family members of the patient, friends of the patient, spiritual advisors of the patient, clergy, caregivers, social workers, and celebrities.

According to a further aspect of the subject technology, the walkie-talkie app is programed and configured to connect to the server over the encrypted data link after a period of non-connection, and then receive and play back voice communications stored on the server.

According to a further aspect of the subject technology, a channel having a channel identifier is established on the server, the channel identifier is provided to the patient and to the persons associated with the patient by a credentialing authority, and the channel identifier is used to establish the voice communication between the patient device and the other devices.

According to a further aspect of the subject technology, the credentialing authority is a hospital.

According to a further aspect of the subject technology, the walkie-talkie app is programmed and configured to display, on the screen, screen identifiers for identifying the patient and the persons associated with the patient.

DETAILED DESCRIPTION OF THE SUBJECT TECHNOLOGY

Figure 1:
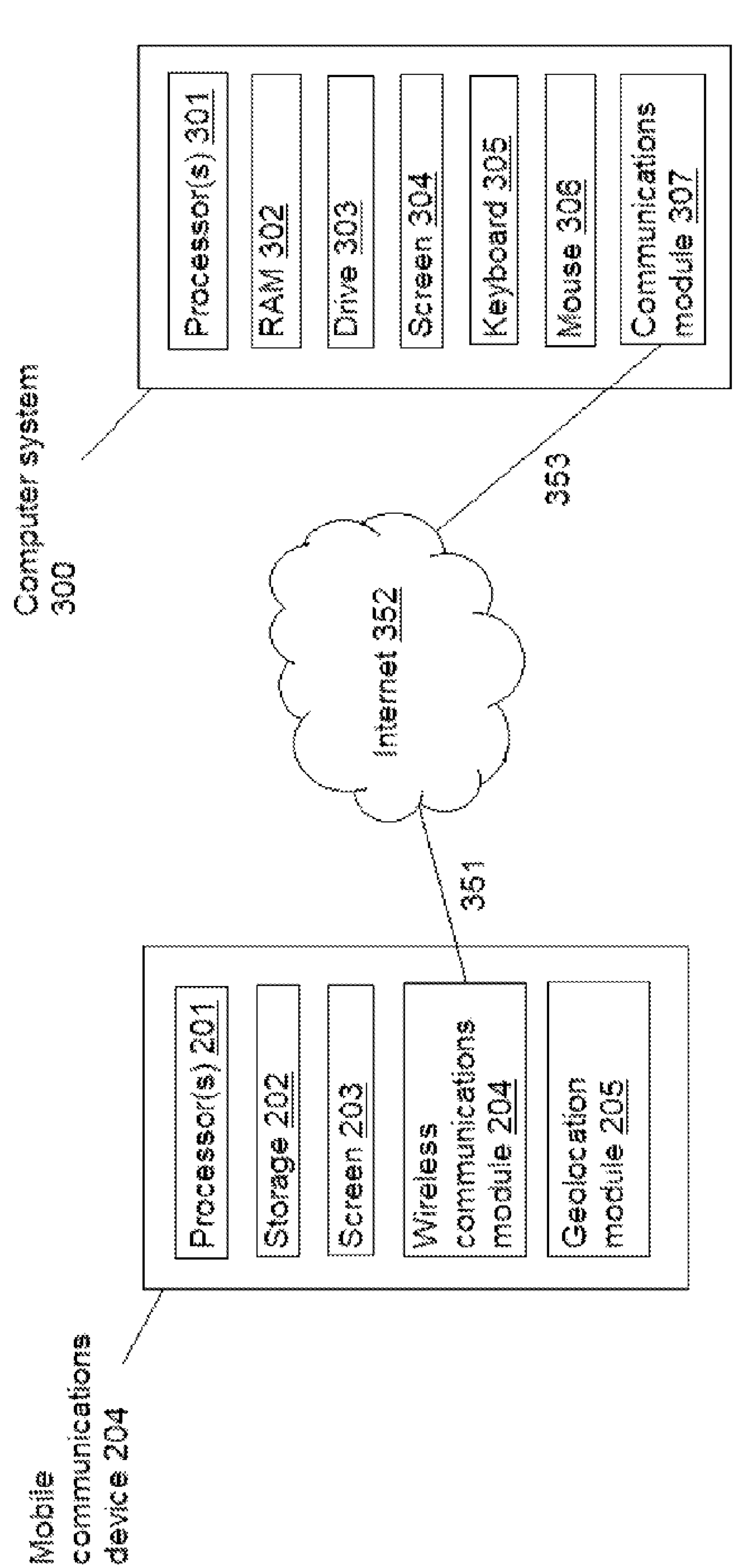
FIG. 1 is a schematic representation of a smart device, back-end server, and data communication link between the smart device and back-end server, according to an embodiment of the subject technology.
Figure 2:
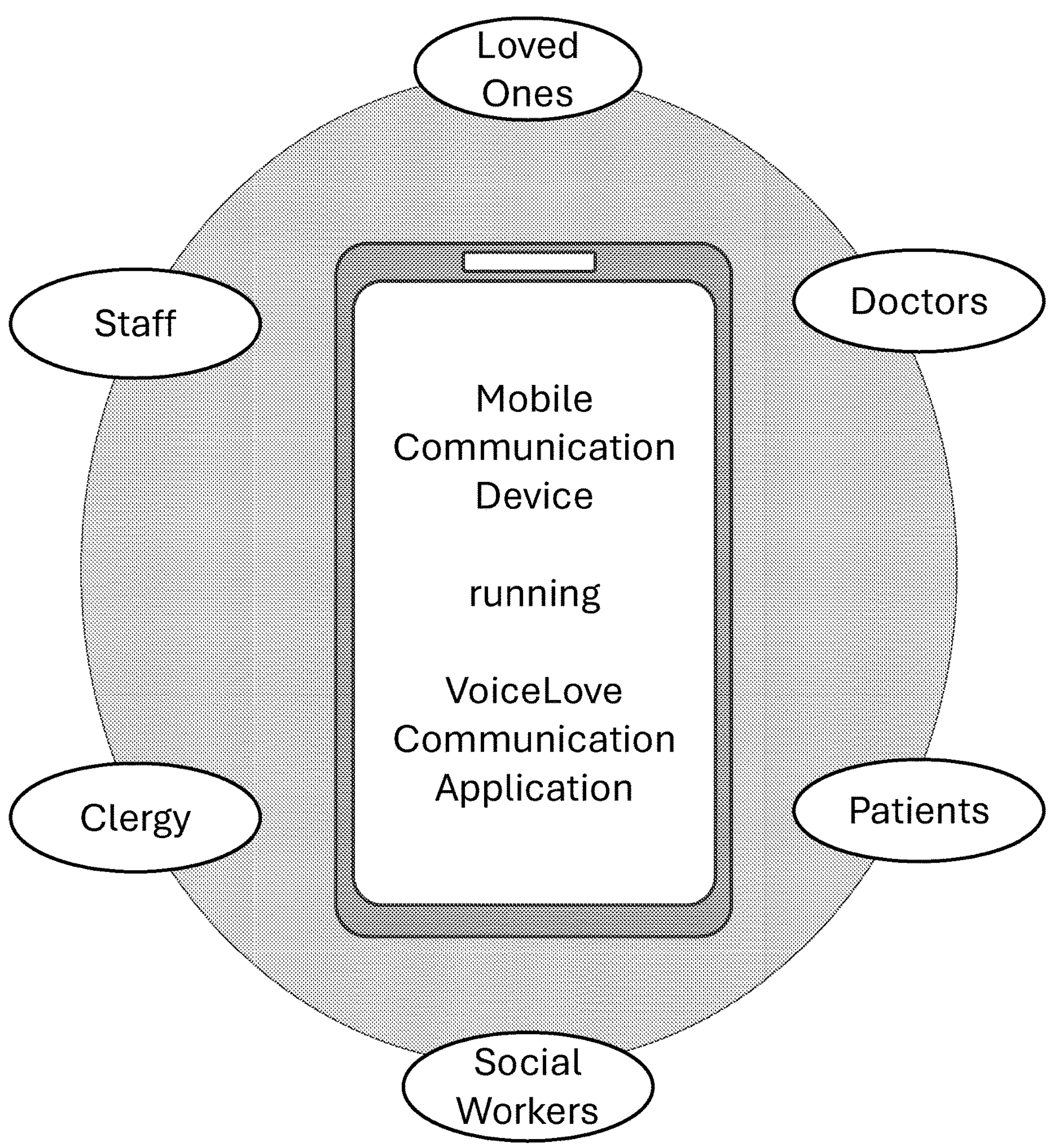
FIG. 2 is a schematic depiction of a device according to an embodiment of the subject technology.
Figure 3:
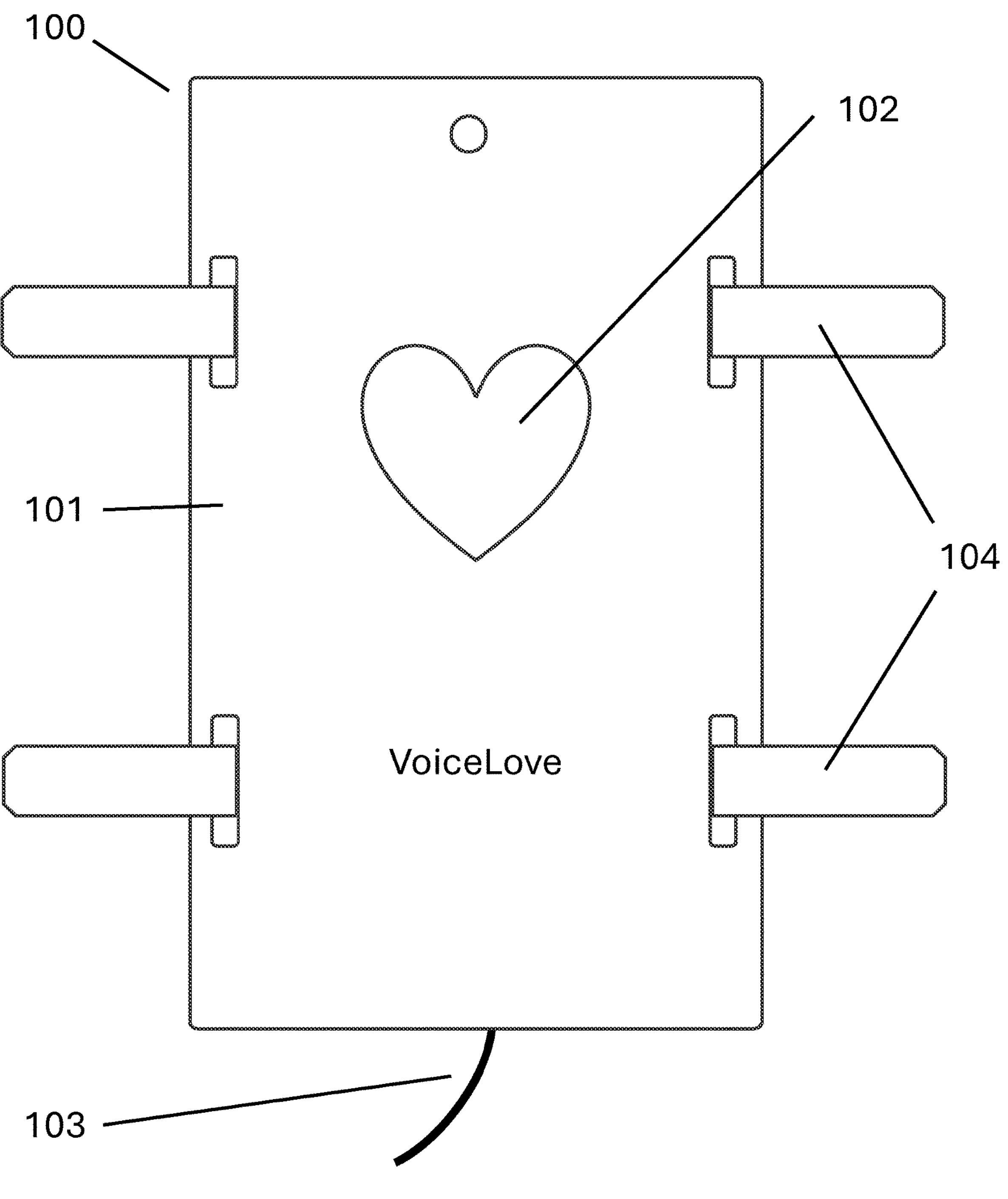
FIG. 3 is a front view of an encased device according to an embodiment of the subject technology.
Figure 4:
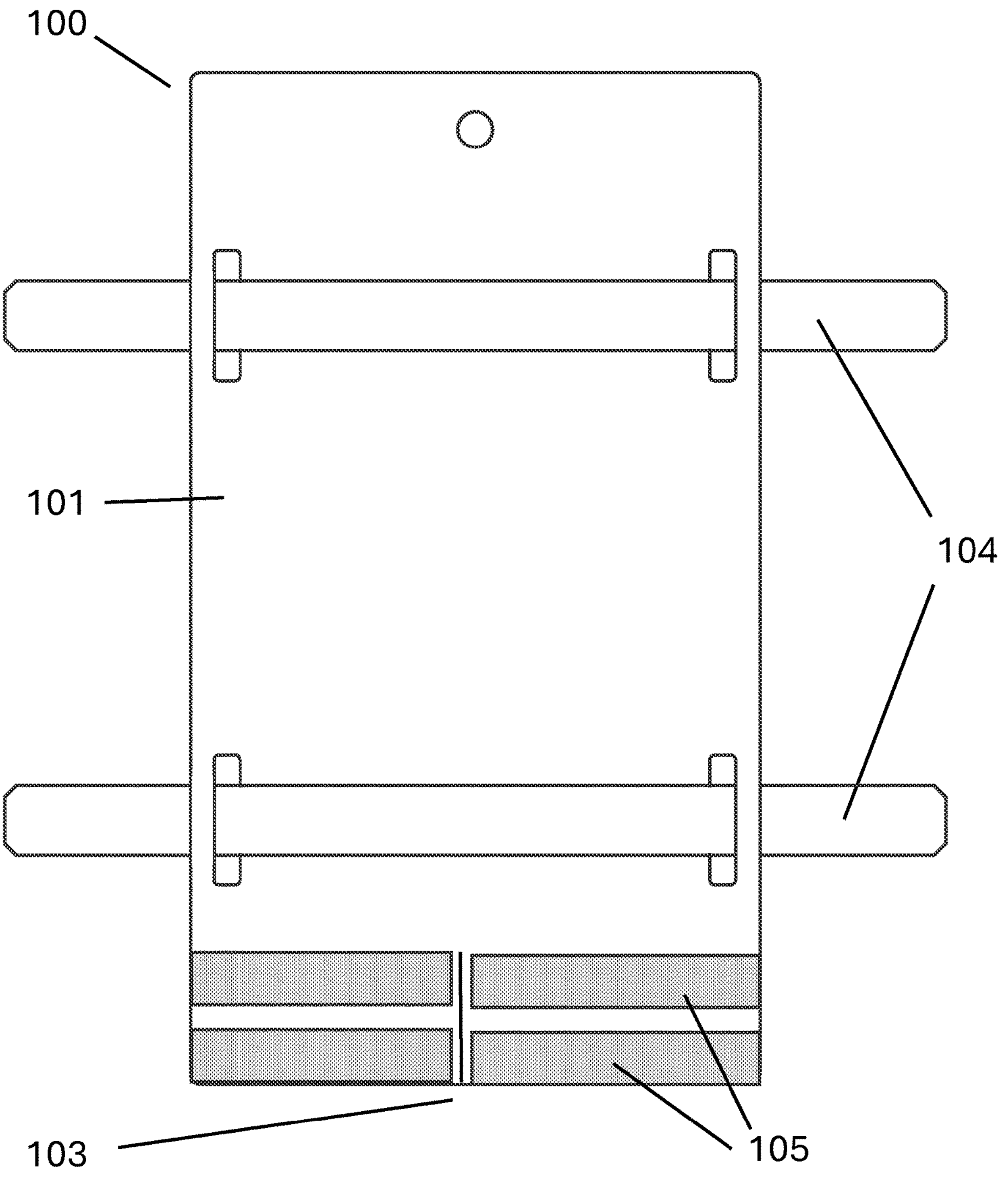
FIG. 4 is a rear view of the encased device of FIG. 3.
Figure 5:
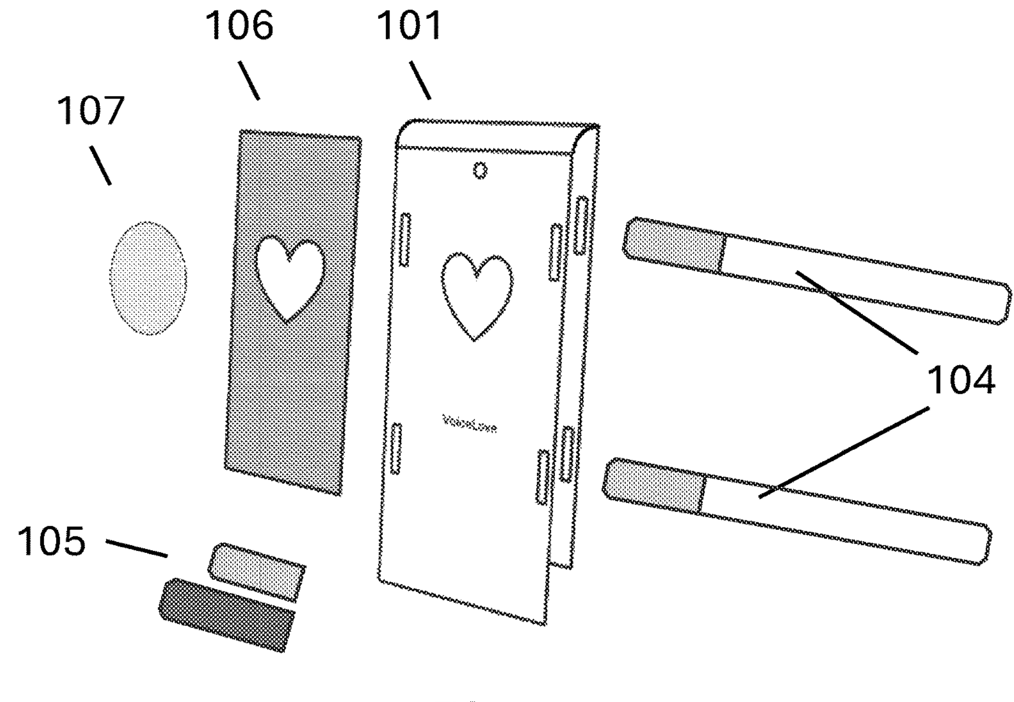
FIG. 5 is an exploded view of a device case according to an embodiment of the subject technology.
Figure 6:
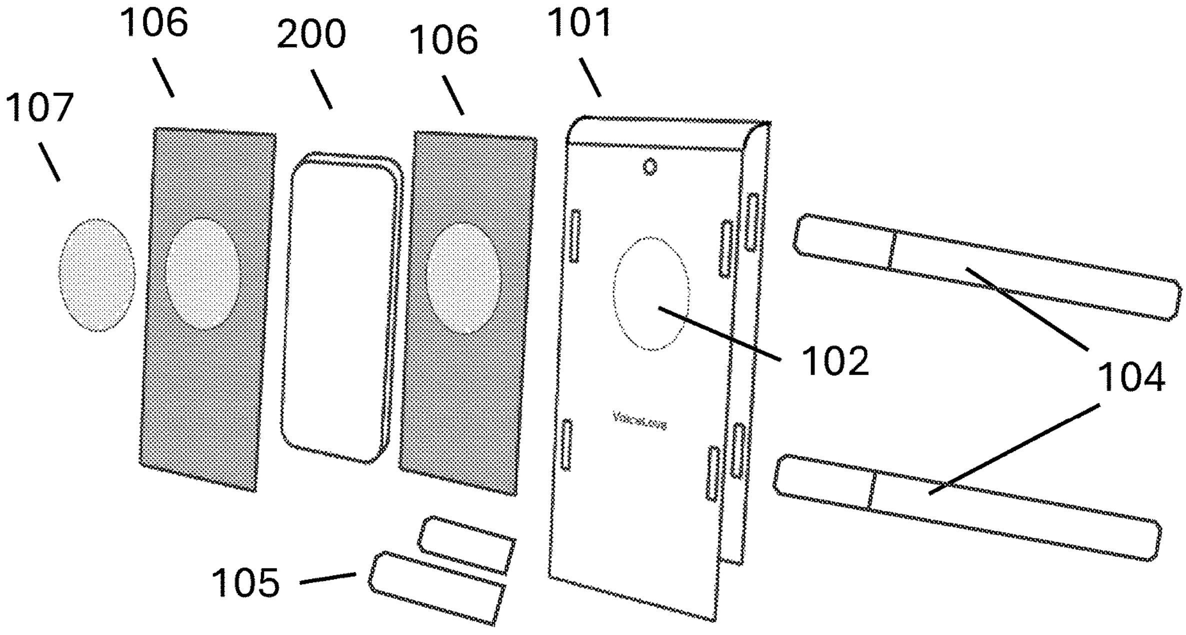
FIG. 6 is an exploded view of a device case according to an embodiment of the subject technology.
Figure 7:
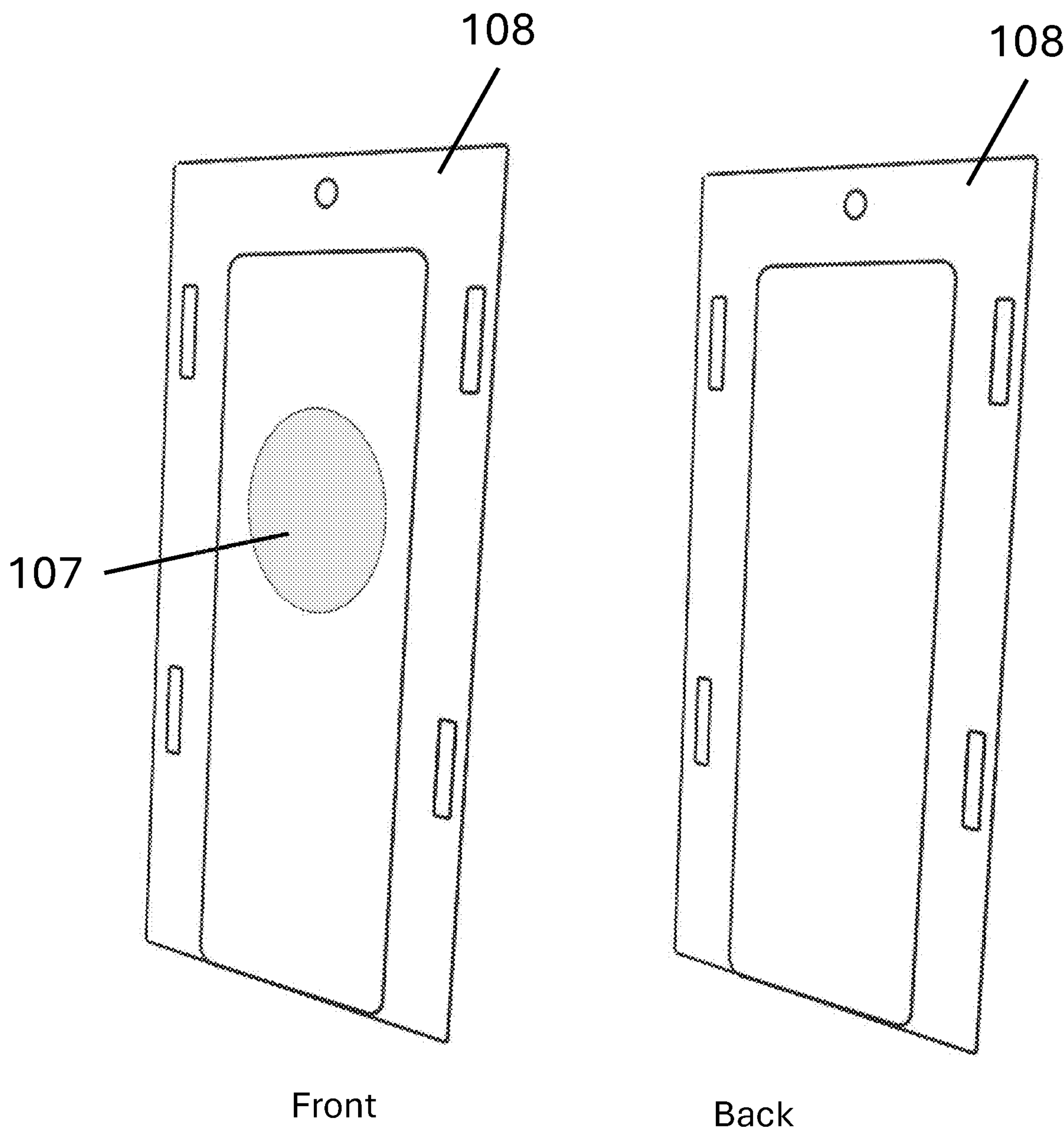
FIG. 7 is front perspective view and a rear perspective view of a device case according to an embodiment of the subject technology.

According to a non-limiting embodiment of the subject technology, a patient in an isolating healthcare environment ("IHE") (for example, an ICU, nursing home, rehabilitation facility, hospice, residential mental health facility, psychiatric hospital, or similar) is provided with a smart device, for example a smart phone, is loaded with an executable communications app, which in a non-limiting embodiment is the VoiceLove walkie-talkie app communicating with the VoiceLove backend servers, hereinafter described. The device is provided within a flexible, biodegradable, anti-bacterial one-use case or envelope, having tapes, ties or similar connectors, to tie attach the device to the patient's bed rail. Or a nearby stand such as an IV pole or other equipment stand, at a position where the patient can touch the device and thereby operate it through the case. The app has at least one input mode ("case mode") in which most or all of the entire screen is functional as a push-to-talk button for operating the app. The case has a raised tactile feature for helping the patient find the push-to-talk button, even if the patient is visually impaired or completely blind. The patient is thereby connected to other authorized users of the VoiceLove walkie-talkie app and servers, including family, friends, clergy, social workers, medical professionals, hospital staff, caregivers, celebrities, and other interested persons. The existence of this connection between the IHE patient and the other authorized users, allowing the patient to hear their familiar voices at any time during the IHE stay, mitigates the effect of the IHE environment on the patient, and thereby reduces the prevalence of delirium and subsequent dementia and/or agitation that may occur due to the IHE environment. The inventors have found, surprisingly, that IHE patients with significant challenges such as reduced visual functioning and/or being on mechanical ventilation are able to communicate using the device.

In a non-limiting embodiment of the subject technology, the VoiceLove smart device application and supporting backend services are programmed and configured as follows.

The VoiceLove app is a React Native application, developed simultaneously for Android and iOS. The application communicates using standard web protocols over Hypertext Transfer Protocol Secure (HTTPS) with the server-side application programming interfaces (APIs). Audio is transmitted real-time using Web Real-Time Communication (WebRTC; a free and open source project) and offline over HTTPS. When installed, this application allows the user to choose "Full Mode" or "One Button", depending on the intended use. "One Button" mode turns the entire device screen into a single button use as the "push to talk button." This screen can be locked with Android app pinning or by using mobile device management (MDM) software in a scenario where VoiceLove or an institution (hospital or other care facility) is deploying devices. The VoiceLove API was developed using Node.Js and the Express.js framework.

The app is backed by a MySQL database (an open-source relational database management system). The application communicates with the API to access settings, pair devices, initiate real-time audio, and send/retrieve audio recordings. A STUN/TURN server supports WebRTC to navigate disparate network environments (i.e., connecting through different IP networks where firewalls and network address translators prevent RTC communications). The open-source STUN/TURN package Coturn is deployed on an Internet-connected server. The open-source platform Kurento is used to support recording WebRTC sessions, transcoding, and other WebRTC services. Data is stored in a MySQL database. The database stores information about device pairings, audio sessions, and audio recordings. The data is encrypted at rest.

These back-end services may be hosted, for example, on cloud-based server platforms. For example, in the non-limiting embodiment of VoiceLove, the back-end services are hosted on Amazon Web Services as follows: 1) VoiceLove API—EC2 Instance 2) STUN/TURN Server—EC2 Instance 3) Kurento Server—EC2 Instance 4) MySQL Database—RDS Instance.

Security and privacy features of this non-limiting embodiment include: 1) all communications to and from the applications and servers are encrypted, 2) all patient information is encrypted at rest, 3) all access is logged and authenticated, and 4) a signed Business Associate Agreement with Amazon confers HIPPA compliance.

As shown for example in the embodiments of the Figures, a hospitalized patient is provided with a communication device which is configured and adapted to implement the system and method of the subject technology. In an embodiment, the communication device is a programmable smart phone, smart tablet, smart watch or other such mobile, Internet-connected device operable by touching a touch screen, the device also having a speaker and microphone (i.e. a "smart device"). In an embodiment, a smart device has loaded thereon and runs an app which is programmed, configured, and adapted to implement the system and method of the subject technology. In an embodiment, the smart device is the patient's own device. In an embodiment, the smart device is provided by the hospital. In an embodiment, the smart device is "bricked" or locked so that only the app of the subject technology and other essential functions may be carried out on the smart device.

The smart device at bedside for use by the patient shall be called the "patient device," smart devices provided by or for other users of the system and method to communicate with the patient shall be called the "user devices."

In an embodiment, the patient device is deployed at the patient's bedside and is contained within a case, sleeve, pouch, or envelope (the "enclosure"). The enclosure has connecting structure such as ties, tapes, hanging rings, or clips to attach itself and the enclosed patient device to a bed rail, within reach of the patient. In an embodiment, the enclosure is provided by the hospital or clinic, and is anti-bacterial, disposable and/or sterilizable to help maintain sterile conditions. The enclosure is adapted to permit the patient to view and operate the patient device while it remains attached to the bed rail. The enclosure is made of material which will pass through the patient's touches to the touchscreen of the patient device to operate the device. The enclosure may be entirely transparent or may be partly transparent (for example, the enclosure may have a transparent window overlying the touchscreen of the patient device, revealing the touchscreen entirely or partially). A small port may be provided in the enclosure for admission of a power cord to charge the patient device. The enclosure is preferably sealable by an adhesive flap or other sealable structure. The enclosure may be in the form of a sealable envelope of flexible material. The enclosure may be in the form of a rigid case, which may include padding on the inner walls thereof to snugly hold the patient device.

The patient device and user devices are programmed, adapted and configured for two-way communication over the Internet with a server or servers (the "server," it will be understood that a single server, a cluster of servers, a virtual server or servers, and cloud server or servers are embraced by this term) also programmed, adapted and configured to carry out the system and method of the subject technology. The programming of the patient and user devices may be in the form of a downloadable app. Preferably, the two-way communications between the server and the devices is encrypted end-to-end, using for example the HTTPS protocol.

The server stores or has access to a database for data storage, as further described. The server also is also programmed, adapted and configured to have a facility for configuring the server, for example, by a password-protected web page, configuration app, or other such means.

In an embodiment, a credentialing authority (the "authority"), such as a hospital, controls access to the system. Preferably, if the server is not on the authority's premises and within its control, the authority has a current business associate agreement ("BAA") with the entity hosting the server (such as a web services company) for privacy regulatory compliance including HIPPA compliance.

The authority configures (or directs a system manager to configure) the server. A configuration of the server includes configuring an organization (such as a hospital or clinic), one or more channels associated with the organization, and one or more users credentialed with the organization, which are represented in the server's database.

A patient and an associated group of users (for example, family members of the patient) are granted the ability to use the system through an "onboarding" process. The on-boarding can be self-directed, wherein users create an account with an email address and then create or join channels. Creating a channel as an individual user requires an in-app purchase or a promo code. Alternatively, users register with an organization using a randomized code that is assigned to each authority, for example an organization (e.g., a hospital). Once registered with an organization, the device is then assigned to the organization. The user is assigned a newly created channel which is paid for by the organizations billing plan. The device then shows up in the organization's inventory of assigned devices (in the administration portal) and may be managed by organization staff. The organization can reassign the device to a new patient or room or remove the device from inventory. Push notifications and API calls then update the device to the new state. The authority also credentializes a patient and an associated group of users (for example, family members of the patient) by, for example, verifying the identity and relationship of the patient and users, and assigning a channel to them which is identified by a unique identifier, and optionally providing a password or passwords to permit access to the channel. Metadata concerning a patient and/or use may be stored in the database such as a unique user ID, the respective familial relationships, patient's room number, unique device ID, and similar metadata. The authority may use the server to generate a pairing code for a particular channel, and provide the pairing code to patient(s) and user(s). The device app is programmed, configured and adapted to receive the pairing code as an input and communicate with the server to register the patient/user and device to the particular channel.

The app of the system and method is downloaded or already present on the patient device and user devices. The patient device is placed within an enclosure and the enclosed device is disposed at the patient's bedside, for example, by tying the enclosure to the patient's bedrail.

In an embodiment, the app is programmed, adapted and configured to have one or more modes of operation including an "in-case" mode for use especially when the patient device is placed in the enclosure. This mode is intended for user in settings where the user is experiencing impaired mobility or cognizance and the mobile device is placed near them for simple communication with their loved ones. The user can cause the application to enter "in-case mode" through a setting. Once in this mode, the entirety, or the majority, of the user interface on the device screen is replaced with one large push-to-talk button, and any sleep function of the device is suppressed, so the device remains on and responsive to activation by the patient. The patient can press anywhere on the screen and begin speaking to send a message to their current channel. In this mode, any messages that are received will automatically play back. Thus, when in use in the in-case mode, the device is safely stored within the enclosure, within reach of the patient, who can easily operate the patient device by touching the large touchable button through the enclosure, during which touching the app is configured to listen to the patient's voice via the on-board microphone, and communicate the voice to the server and on to other users, as will be described.

Similarly, the user devices will download and run an app that is programmed, configured, and adapted to connect over the Internet to the server, log in using the provided credentials, and interact with the assigned channel. The app on the user devices may display operational buttons such as push-to-talk, conversation mode (which would not require the button to be pressed continuously), and mute (i.e. listen to the channel but not use the device microphone to record and send voice data via the channel).

The patient device and user devices are thus programmed, adapted and configured to record and play back the voices of the persons using the respective devices, which voices are digitized and encoded, and sent to the server via the Internet. Upon receiving an incoming voice message from a device connected to the channel, the server then replays the voice message to the other devices connected to the same channel, which may be in real-time, thereby achieving two-way voice communication.

The app may also be programmed, adapted and configured to display the identities of the persons currently authorized to the channel and their status (such as on-line and available for two-way communications, muted (listening but not recording), or off-line). When in in-case mode, this feature may be suppressed, because the touchscreen (or a portion of it) may not be visible.

The server is preferably programmed, configured and adapted to send "push" notifications or similar to the devices associated with a channel, when for example a person logs in to the channel or logs out from the channel, or in similar events.

It is contemplated that the patient device and authorized user devices will connect via the server, to the assigned channel, from time to time. That is, the patient and user devices are not necessary connected to the assigned channel at all times. To accommodate these changes from time to time, the server may be programmed, adapted and configured to store incoming voice communications together with metadata including the time of the communication, and who has heard the communication (i.e., which patient and/or user devices have had the voice message sent to them by the server). When a patient or user connects to the channel after a period of absence, the server may send any stored, unheard voice messages to the patient or user, thereby effecting a "catch-up mode." Alternatively, the app may display a list of missed voice messages and associated metadata (e.g., patient, user, time) and play back a missed message by operation of the touch screen. Voice messages may expire and be deleted after an amount of time has passed since the time of the communication, for example, after 24 hours. Preferably, any stored voice messages are securely encrypted and stored in the server database in the encrypted form, which will necessitate decryption before sending the voice messages to a connected device. After the catch-up mode, the server then reverts to the near real-time communication between the currently connected devices.

Preferably, all access to the system or any individual channel will be properly authenticated and logged for inspection and auditing by or on behalf of the authority.

The system and method of the subject technology may be applied in other institutional settings, for example, the staff of a medical institution may be provided the app for their own devices, or provided with dedicated, locked or "bricked" smart devices programmed with the app of the subject technology, and the necessary credentials to log into the server and communicate with channels as may be appropriate for their staff functions. Possible applications include: providing a channel for the custodial staff of a hospital to communicate; providing a channel for a surgeon or other operator to communicate with colleagues during a procedure; providing hospital security staff with a channel to communicate during their shift; and similar applications.

In an embodiment the server and app may be under the control of and provided by a service provider. The service provider may enroll hospitals and other institutions to use the system and method. The provider may allocate a certain number of codes to the enrolled institutions, each code enabling the institution to configure one patient or user in the system. Commercially, the provider may offer codes for purchase or on a subscription model, when for a periodic fee the institution is allocated a certain number of codes for that period (e.g., 1000 codes a month).

As shown for example in the Figures, an exemplary embodiment of the subject technology is as follows. It will be understood by those of skill in the art that the exemplary embodiment may be varied, adapted and/or extended with additional features, structures and functions as previously described herein.

As shown for example in FIG. 1, mobile communication device 204 is a programmable computing device comprising one or more processors 201, operably associated with digital memory storage 202 for storing data on the device 204, a user interface touch screen 203 for presenting information and receiving information from a user, a wireless communications module 204 (for example a cellular radio) for connecting wirelessly to one or more cellular communication towers and/or the Internet, and a geolocation module 205 (for example, a GPS module) for determining the current location of device 204. Mobile communication device 204 may be, for example, a smart device, smartphone, smart table, or other mobile device having similar functionality, known to the art.

According to a further aspect of an embodiment of the subject technology, as shown in FIG. 1, a server 300 is provided. Server 300 is programmable for data acquisition, storage, processing and output, according to the present disclosure. Server 300 may comprises one or more one or more processors 301, operably associated with digital memory storage for short-term (e.g. RAM 302) or long-term (e.g. fixed disk drive or solid state drive 303) storage of data on the device 204, a user interface screen 304 for presenting information and receiving information from a user, a keyboard 305 and mouse 306 for receiving information from a user, a digital communications module 307 (for example a cellular radio or network card) for communicating with other digital devices, ultimately via the internet, and may further be operably associated with other computing peripheral devices such as printer(s), scanner(s), etc. as known in the art. In a preferred embodiment of the subject technology, server 300 is a virtualized cloud-based server instance, for example, an Amazon EC2 instance.

Device 204 and server 300 are in data communication contact, at least part of the time, and can mutually send, receive and communicate digital data through a data link, which may be comprised of one or more data connection segments, for example, a cellular data communication segment 351 between device 204 and the Internet 352, and a wired or wireless data communication segment 353 from the internet 352 to server 300. Device 204 and server 300 are programmed and configured to interoperate and implement the features and functions described in more detail herein.

Some patients may have the capacity to hold, manipulate and use device 204 as they normally would use such a device. However, according to an important aspect of the subject technology, a case for enclosing device 204 is provided, with features to facilitate the use of the device by a patient in an isolating hospital environment, who may have limited capacity.

In an embodiment, case 100 comprises envelope 101 made of flexible polymer film, sealed on the top, left and right edges thereof (or alternatively, folded in half to form the top edge, and sealed on the left and right edges thereof), and open and sealable on a bottom thereof for insertion of device 204. A transparent window 102 is provided in envelope 101 for visibility of the device 204 within case 100. At least the window 102 of envelope 101 is made of a material which will pass touches through to the underlying screen of device 204. Straps 104 having hook-and-loop fasteners thereon are passed through slots on envelope 101, thereby providing a structure for removably fastening case 100 to a bed rail or other structure near the patient, for easy access to and operation of device 204. The open bottom edge of envelope 101 is sealable by adhesive strips 105. A port 103 is provided in the bottom edge of envelope 101 for passage of a charging cord, to keep device 204 charged and powered on for use by the patient. In embodiments, one or two padded inserts 106 may be provided within envelope 101 to provide cushioning of device 204. In embodiments, a hard tactile button 107 may be provided in association with window 102, by which the patient may operate device 204. Alternatively, a ridge or other tactile feature 109 may be formed in envelope 101 surrounding window 102. In either case, these tangible features of case 100 assist the patient in locating and operating the push-to-talk functionality of device 204. In an alternative embodiment, hard polymer shell 108 is used in place of envelope 101.

When use of case 100 is appropriate with a given patient, device 204 is powered on and the app of the subject technology is launched, and is activated to place the device and app in "in-case mode." In this mode, the sleep or power-off function of device 204 is suppressed, and the entire screen, or substantially the entire screen, is activated to be a push-to-talk button. The screen is visible through window 102, which is surrounded by a tactile ridge so it may be located by feel. Device 204 is placed within case 100, and preferably device 204 is connected to a power source via a charging cord passed through port 103. Case 100 (with device 204 within) is attached in a convenient place for the patient, such as being tied to the bedrail, within reach of the patient, by straps 104. It should be appreciated that these steps can be carried out by hospital staff.

Turning now to the functionality of the system of the subject technology, device 204 and server 300 are programed and configured to interoperate as follows. Broadly speaking, the subject technology involves several phases of operation: 1. Establishing an authority; 2. On-boarding users; 3. Communication between users.

In the first phase of establishing an authority, data ("authority data") which identifies a hospital, facility, clinic, organization, or other credentialing authority is inputted into the data storage of server 300, via an interactive website, through the device app, or otherwise. Authority data may include, for example, the name and physical address of the authority and a randomized organization key which uniquely identifies the authority in server 300.

Authority data may further include an allotment of a number of channels which the authority is entitled to create for use by end-users. The number of channels may be a function of the authority's tier of service (for example, an unpaid tier of service may include a fixed number of channels, for example 200, while paid tiers of service may permit greater numbers of channels, or an unlimited number of channels, to be created by the authority.)

Once an authority has been established, the authority may create one or more channels for communications use, up to the allotted number of channels. Each channel is associated with the authority and is identified by an ID number, which may be a serial number, and a unique channel code, which may be a random or partially random string of words, letters and/or numbers. Channel codes are provided to users of the subject technology to pair their devices with the corresponding channel, as will be explained.

In the onboarding phase, users of the subject technology are registered as such. User-identifying data, for example, the user's first and last name, email address, phone number, facility room number, photo, and a password, are collected and stored in the data storage of server 300. During this phase, the user provides at least one channel code which has been provided to the user by the authority, corresponding to at least one channel created by the authority. This data may be collected and stored by the authority or may be provided by the user using the app of the subject technology. It should be understood that a patient in an IHE is an intended user, additionally, other persons associated with the patient will be users, for example, family members, healthcare providers, social workers, spiritual advisors, celebrities, and other persons. All of these associated users would be provided the same channel code, using the same channel to communicate as will be described.

In the communication phase, users use their respective devices for voice communication in the channel. When connecting to a channel, the server 300 is programmed to check for previously saved voice messages in the channel which have not been delivered to the connecting user. (As will be explained, incoming voice messages are stored for later playback.) Playback of such previously saved voice messages in a "catch-up mode" may be suppressed on a channel-wide or per-user basis, or optionally the app may display a checkbox upon connecting to permit the user the option of suppressing catch-up messages in this instance. If "catch-up mode" is not suppressed for this channel, this user, and this instance of connecting to the channel, the server 300 will playback any previously unheard messages by data communication to the user's device 204. In this instance, and all other instances of voice communication in the subject technology, the data link between server 300 and device 204 is encrypted end-to-end, by, for example, HTTPS encryption.

Figure 8:
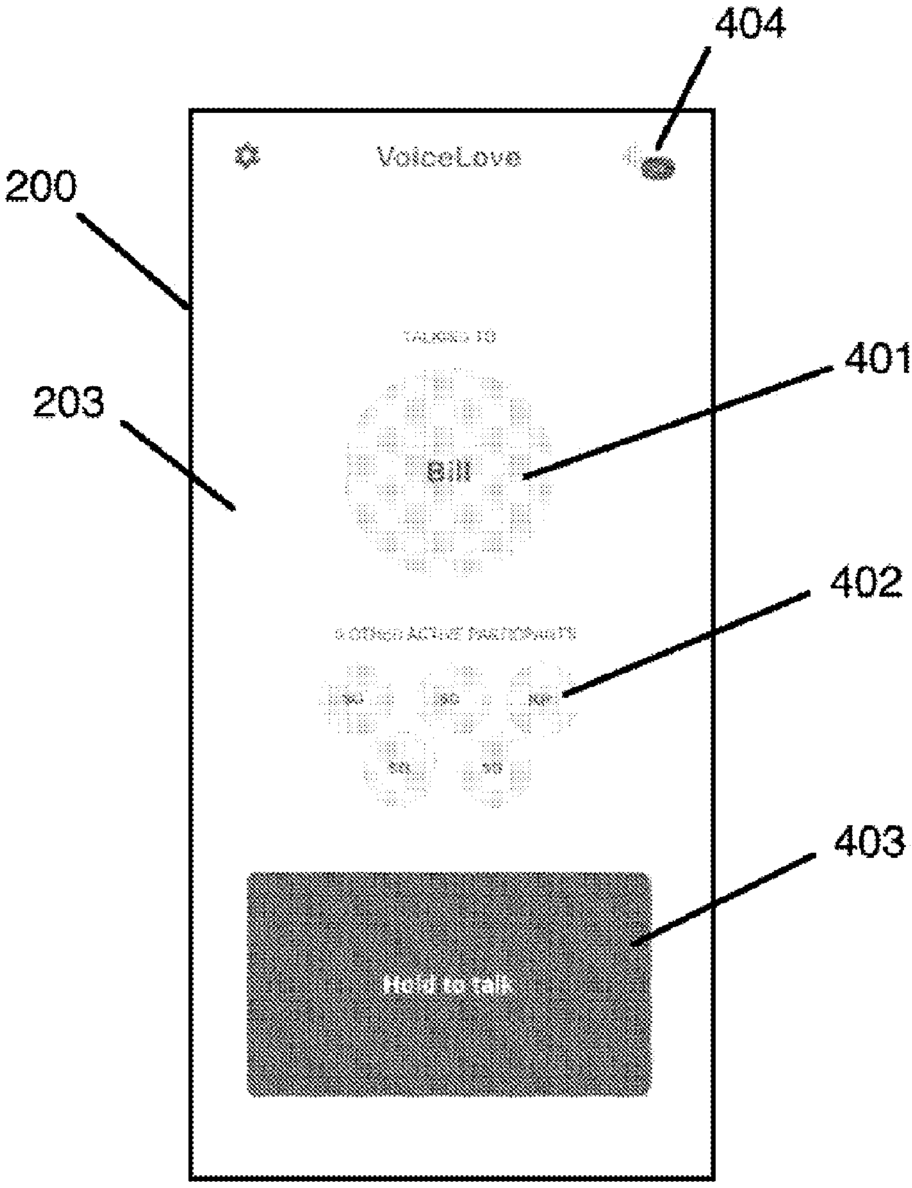
FIG. 8 is a rendering of a device in default communication mode according to according to an embodiment of the subject technology.

While connected to a channel, the app running on device 204 is configured to interact with server 300 in a variety of modes of operation. In a default mode, while connected to a channel, as shown for example in FIG. 8, the screen 203 displays a screen identifier 401 of the patient for whom the channel is dedicated (an screen identifier is a user's name, initials, and/or photo). The screen 203 also displays screen identifiers 402 of all other persons connected to the channel. The screen 203 displays operational buttons, including a push-to-talk button 403, and a catch-up button 404. Pressing catch-up button 404 causes device 204 to display a list of any unplayed voice messages in this channel stored on server 300, which may be selected off the list for playback on device 204. Pressing and holding push-to-talk button 403 causes device 204 to record a voice message using the microphone of device 204, which is stored in data storage on device 204 in a digital audio format, for example, AAC format. Releasing push-to-talk button 403 causes device 204 to transmit the stored voice message over the encrypted data link to server 300, where it is stored and associated with the channel.

Upon receiving and storing a voice message from device 204, server 300 sends a push notification to all devices (or, optionally, a user-selected subset of all devices) currently connected to the channel. The voice message is transmitted over the encrypted data link and played back on all connected devices (or the user-selected subset of devices), and the screen identifier of the speaking user is highlighted to identify the user who created the message being played back. The voice message continues to be stored on server 300 for later playback on devices which join the channel later.

Figure 9:
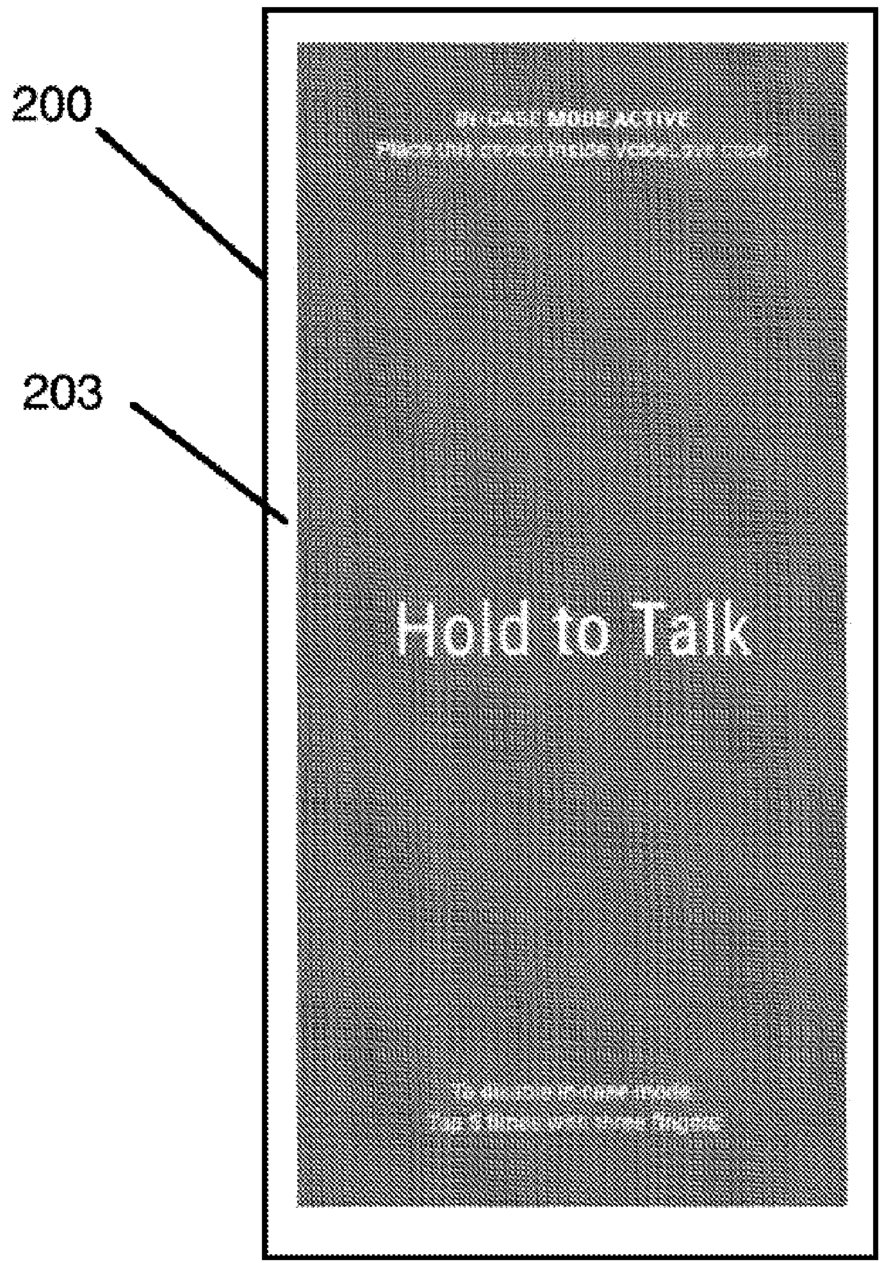
FIG. 9 is a rendering of a device in in-case mode according to according to an embodiment of the subject technology.

In addition to the default mode, which may be difficult for a hospitalized patient to operate, the app running on device 204 is also configured and programmed to operate in an in-case mode. When this mode is selected, the entire screen 203 (or substantially the entire screen) is used as a push-to-talk button, as shown for example in FIG. 9. The device 204 is encased in case 100 and disposed in a convenient place for the patient to operate it, as previously described. While in in-case mode, any received voice messages from server 300 are played back automatically.

Figure 10:
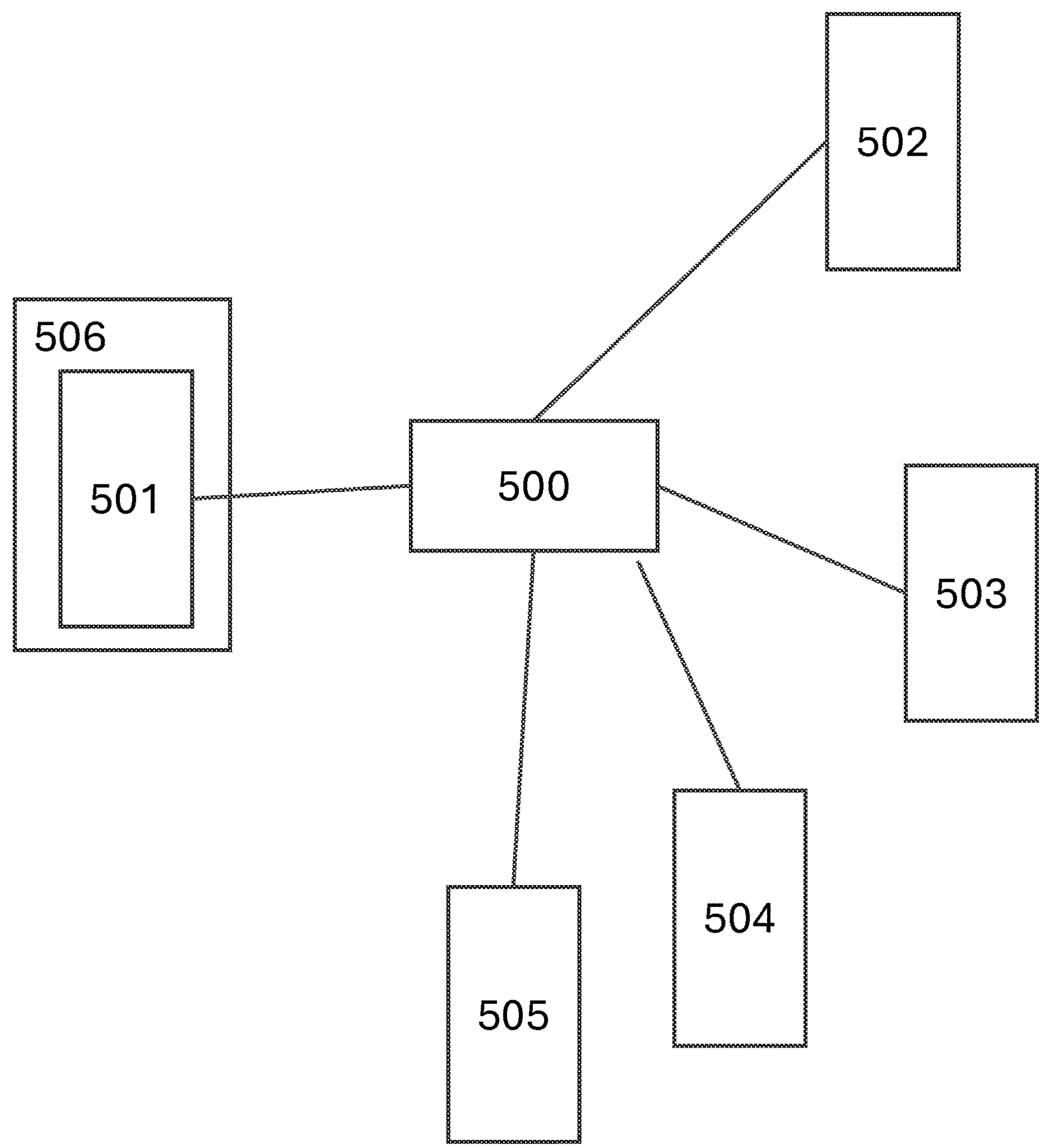
FIG. 10 is a schematic of devices connected to a server according to an embodiment of the subject technology.

According to an aspect of the subject technology, as shown in FIG. 10, devices 501, 502, 503, 504, 505 are smart devices having an executable walkie-talkie app thereon as previously described. Device 501 is in a case 506 adapted to be disposed near a patient in an isolating hospital environment, which case 506 may be a specially adapted case 100 as previously described in various embodiments. Devices 502, 503, 504, 505 are each used by a person associated with the patient. For example, device 502 is used by a family member, 503 is used by a social worker, 504 is used by a well-wisher, 505 is used by a member of clergy. Devices 502, 503, 504, 505 are each connected to server 500 over encrypted Internet data links represented by lines (unnumbered). Server 500 is configured and programmed to receive, store, and transmit voice messages between devices 502, 503, 504, 505, as the backend processor of the VoiceLove technology as previously described. In this manner, the patient can hear the voices of the persons associated with the patient, which will be effective to mitigate the delirium-causing effects of the isolated hospital environment.

The foregoing system is deployed clinically to prevent, reduce, or mitigate the tendency of patients in an IHE environment to suffer from dementia, agitation, or other mental degradation due to the IHE environment. By deployment and use of the subject technology, patients in an IHE environment have a convenient and effective means to communicate with family members, loved ones, advisors, clergy, friends, caregivers, social workers, celebrities, and other persons supporting the patient. As previously described, this "Family engagement and empowerment" is a factor in mitigating the mental effects of the IHE environment. The subject technology can be deployed at a patient's bedside with minimal involvement of hospital staff.

While specific embodiments of the subject technology have been shown and described in detail to illustrate the application of the principles of the subject technology, it will be understood that the invention may be embodied otherwise without departing from such principles. It will also be understood that the present subject technology includes any combination of the features and elements disclosed herein and any combination of equivalent features. The exemplary embodiments shown herein are presented for the purposes of illustration only and are not meant to limit the scope of the subject technology.

What is claimed is:

1. A method of preventing, reducing, or mitigating hospital-acquired delirium of a patient in an isolating healthcare environment, the method comprising the steps of:

providing a patient device to the patient enabling voice communication between the patient and persons associated with the patient, the patient device comprising:

a speaker for playing voice communications;

a microphone for recording of voice communication;

at least one computer having at least one CPU and a memory;

at least one touch screen;

one or more sensors; and software communicating over one of an encrypted channel and a nonencrypted channel ("Patient App") to software running on a remote computer ("User App");

wherein the patient device has a mode that, when actuated, causes the at least one touch screen to function as a single button;

wherein the Patient App and User App may be either a same software or a different software;

actuating the mode to disable the one or more sensors;

recording by the patient device, when the single button is actuated by the patient, one or more voice messages;

sending the one or more voice messages to the User App;

determining, by the patient device, whether it has received one or more audio messages, and if so, playing back the one or more audio messages.

2. The method of claim 1, wherein the patient device further comprises a specialized case and at least a portion of the specialized case is:

connected to one or more of a bed rail, an equipment stand, and an IV holder;

constructed of a flexible material;

sterilized prior to use; and equipped with a transmissive material overlaying at least a portion of the at least one touch screen, wherein the transmissive material allows actuation of the at least one touch screen.

3. The method of claim 2, wherein the specialized case has a port through which a charging cord is connected.

4. The method of claim 1, wherein the patient device has a geolocation module that determines a geographic location of the patient device, and one or more functions of the patient device are altered based on the geographic location.

* * * * *